United States Patent [19]

Connor et al.

[11] Patent Number: 5,298,636

[45] Date of Patent: Mar. 29, 1994

[54] PROCESS FOR REDUCING THE LEVELS OF UNREACTED AMINO POLYOL CONTAMINANTS IN POLYHYDROXY FATTY ACID AMIDE SURFACTANTS

[75] Inventors: Daniel S. Connor; Mark Hsiang-Kuen Mao, both of Cincinnati, Ohio

[73] Assignee: The Procter & Gamble Company, Cincinnati, Ohio

[21] Appl. No.: 950,390

[22] Filed: Sep. 23, 1992

[51] Int. Cl.$^5$ ............................................. C07C 231/00
[52] U.S. Cl. ......................................... 554/70; 554/66; 554/68; 554/69; 252/544
[58] Field of Search ................... 554/68, 66, 69, 70; 252/544

[56] References Cited

U.S. PATENT DOCUMENTS

| | | | |
|---|---|---|---|
| 1,985,424 | 12/1934 | Piggott | 260/124 |
| 2,016,962 | 10/1935 | Flint et al. | 260/127 |
| 2,429,445 | 10/1947 | Young et al. | 554/66 |
| 2,638,449 | 5/1953 | White et al. | 554/66 |
| 2,703,798 | 3/1955 | Schwartz | 554/66 |

FOREIGN PATENT DOCUMENTS

| | | | |
|---|---|---|---|
| 0220676 | 5/1987 | European Pat. Off. | C07C 103/38 |
| 3-246265 | 11/1991 | Japan | C07C 233/18 |

*Primary Examiner*—José G. Dees
*Assistant Examiner*—D. Carr
*Attorney, Agent, or Firm*—Jerry J. Yetter; Donald E. Hasse; Ronald L. Hemingway

[57] ABSTRACT

Polyhydroxy amines reacted with fatty acid esters yield polyhydroxy fatty acid amide surfactants, such as the $C_{11}$–$C_{17}$ fatty N-methyl glucamides, which may be contaminated with secondary amines. Such amines are acylated by a reaction with acetic anhydride. The resulting "clean" polyhydroxy fatty acid amide surfactants are preferred for use in the presence of oxidants, especially in the formulation of modern, colorless liquid detergents.

5 Claims, No Drawings

PROCESS FOR REDUCING THE LEVELS OF UNREACTED AMINO POLYOL CONTAMINANTS IN POLYHYDROXY FATTY ACID AMIDE SURFACTANTS

FIELD OF THE INVENTION

The present invention relates to an improvement in a chemical reaction for preparing polyhydroxy fatty acid amide surfactants, whereby the content of unreacted amino polyol contaminants is reduced or substantially eliminated.

BACKGROUND OF THE INVENTION

The preparation of polyhydroxy fatty acid amide surfactants by the reaction of fatty esters with N-alkylamino polyols is of considerable commercial interest. However, the resulting N-alkylamido polyol reaction products, such as the fatty acid N-methyl glucamides, are often contaminated with residual amounts of unreacted N-alkylamino polyols. Contamination by such materials may be tolerable under many circumstances. For some uses, however, the presence of unreacted N-alkylamino polyols may be undesirable for color and odor reasons. In particular, the manufacturer of modern, clear, colorless, high sudsing detergent compositions which contain polyhydroxy fatty acid amide surfactants (e.g., $C_8$–$C_{22}$ fatty acid amide derivatives of N-methyl glucamine or N-methyl fructamine) requires an inexpensive source of such materials which have desirable low amino polyol levels. In addition, the manufacture of such detergent compositions, especially the colorless versions, sometimes employs various bleaching agents, such as $H_2O_2$, which could potentially oxidize the residual N-alkylamino polyols to undesirable by-products. Manufacturers presumably could arrange for special care to be taken during the reaction in order to minimize the levels of such unreacted starting materials, or employ separate purification techniques. However, the manufacturer of high volume, low-cost chemicals such as home-use detergents can ill-afford special handling techniques or materials which require expensive purification steps.

The present invention solves the heretofore unappreciated problem of contamination by sources of N-alkylamino polyols associated with the manufacture of polyhydroxy fatty acid amides, and thereby affords access to a high quality supply of this class of surfactants which are especially useful in situations where oxidants may be present.

BACKGROUND ART

The following references are instructive: U.S. Pat. Nos. 1,985,424, issued Dec. 25, 1934; 2,016,962, issued Oct. 8, 1935; 2,703,798, issued Mar. 8, 1955; Japanese HEI 3[1991]246265; and EPO 220,676, published Oct. 10, 1986.

SUMMARY OF THE INVENTION

The present invention encompasses, in a process for preparing a primary reaction product comprising a polyhydroxy fatty acid amide surfactant, said primary reaction product containing undesirable amounts of unreacted N-alkylamino polyols, said process comprising a Primary Reaction between an N-alkylamino polyol and a fatty acid ester, said Primary Reaction being carried out at a temperature below about 100° C. so as to minimize formation of cyclized by-products in said reaction product, the improvement which comprises adding to said Primary Reaction product an acid anhydride (especially acid anhydrides such as acetic anhydride, maleic anhydride and succinic anhydride) and subjecting said reaction product to a Secondary Reaction, whereby the total level of unreacted N-alkylamino polyol present in the product of the Secondary Reaction (i.e., in the final, overall product) is substantially eliminated, i.e., reduced to below about 0.2%, by weight, preferably below about 0.1%, by weight.

In a typical and preferred mode, said primary reaction product is prepared by a Primary Reaction of a $C_8$–$C_{22}$ fatty acid ester and an N-alkylamino polyol, especially wherein the fatty acid ester is a methyl ester, and more especially wherein said Primary Reaction is carried out in the presence of a base catalyst, preferably sodium methoxide. In a highly preferred mode, the Primary Reaction is carried out in a nonaqueous hydroxy solvent, especially methanol or 1,2-propanediol, or mixtures thereof, in the presence of an alkoxide catalyst, and in the absence of water. Advantageously, the Primary Reaction can be carried out in the presence of a phase transfer agent, such as a standard ethoxylated nonionic surfactant, e.g., those sold under the trademarks NEODOL and GENEPOL, which provides a homogeneous reaction system.

A convenient process according to this invention is wherein said anhydride reactant used in the Secondary Reaction is a low molecular weight carboxylic acid anhydride, and especially wherein said acid anhydride reactant is acetic anhydride. In some instances, the acetic anhydride may leave a residual odor of acetic acid. Often, this can be handled with a perfume. However, if the acetic acid odor is to be entirely avoided, the formulator can use an anhydride having a lower vapor pressure, e.g., maleic anhydride or succinic anhydride. Preferably, said Secondary Reaction is carried out at a temperature of from about 10° C. to about 85° C. (melt reaction). Preferably, the reaction is carried out at from about 10° C. to about 70° C. (especially when an aqueous solvent is used), more preferably 20° C.–50° C. In a typical mode, the reaction is carried out using about 10 mole percent or more, typically 15 mole percent of the acid anhydride, based on the N-alkyl polyhydroxyamine. Use of an excess of the anhydride is satisfactory and can drive the reaction to completion.

The invention herein thus provides an overall process for preparing high quality polyhydroxy fatty acid amide surfactants, as follows.

(a) A primary amidation reaction is conducted under substantially water-free conditions between a fatty acid ester and an amino polyol, as illustrated by the reaction between $C_{10}$–$C_{18}$ fatty alkyl or alkenyl (especially oleyl) methyl esters and N-methyl glucamine in the presence of an alkoxide catalyst and a polyol and/or alcohol solvent, preferably at temperatures below about 100° C., as follows:

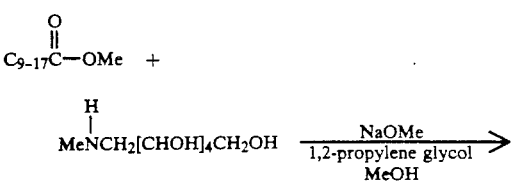

-continued

$$C_9-C_{17}C-NCH_2[CHOH]_4CH_2OH$$

thereby providing the reaction product containing the polyhydroxy fatty acid amide surfactant which is substantially free of cyclized by-products, but which is contaminated with unreacted amino polyol. (This product may also be contaminated with residual nascent fatty acids, which can dampen sudsing. Such fatty acids can optionally be handled by reacting them in an intermediate amidation step, e.g., with a primary alkanolamine, such as monoethanolamine.)

(b) Following step (a), the primary reaction product is reacted with the acid anhydride to acylate residual unreacted amine materials, especially the amino polyol starting materials.

The present invention also encompasses detergent compositions which are in the form of colorless liquids. Such compositions are prepared using the substantially N-alkylamino polyol-free (i.e., below about 0.2% by weight, preferably below about 0.1%, by weight) polyhydroxy fatty acid amides prepared in the foregoing manner plus auxiliary surfactants and possible trace quantities of bleaches, especially $H_2O_2$, which may be required to provide the ingredients used in such compositions, and hence the finished compositions, with their desired colorless appearance.

All percentages, ratios and proportions herein are by weight, unless otherwise specified. The pressures specified herein are gauge pressures.

DETAILED DESCRIPTION OF THE INVENTION

This invention provides an overall process for preparing high quality polyhydroxy fatty acid amide surfactants which are substantially free of contamination by amines, such as the amino polyols, especially the N-alkylamino polyols. Since the process affords the desired surfactants using conventional, mainly renewable resources, the overall process will be described herein in some detail, although the improvement of this invention resides in the reduction of amino polyols in the Secondary Reaction by reaction with short chain acid anhydrides. For high-sudsing compositions the formulator will also wish to remove traces of residual nascent sources of fatty acids, and that step is also provided for in one optional version of the overall reaction sequence disclosed herein. Thus, the disclosure herein provides an overall commercial-type process, beginning with the formation of the N-alkyl polyhydroxy amine, followed by its conversion into the polyhydroxy fatty acid amide in a "Primary Reaction", optionally with reduction in residual nascent fatty acid levels, and by the reduction of residual aminopolyol levels using the technology afforded by the "Secondary Reaction" of the present invention.

As an overall proposition, the process described hereinafter will afford high quality N-alkylamino polyol reactants with desirable low Gardner Color and which are substantially free of nickel catalysts. Such N-alkylamino polyols can then be reacted in, preferably, fatty acid methyl esters to provide high yields (90-98%) of polyhydroxy fatty acid amides having desirable low levels (typically, less than about 0.1%) of cyclized by-products and also with improved color and improved color stability, e.g., Gardner Colors below about 4, preferably between 0 and 2. The content of nascent fatty acids present in the polyhydroxy fatty acid amide is optionally minimized by reaction with primary amines, as disclosed herein. It will be understood that the nascent fatty acids are not thereby removed from the final product, but are converted into amido forms which can be tolerated in finished detergent compositions, even in liquid detergent compositions which contain calcium or magnesium cations. Indeed, by judicious selection of amines such as ethanolamine, the fatty acid monoethanolamides are, themselves, desirable cleaning and suds-boosting ingredients, especially in liquid dishwashing detergents.

Following the Primary Reaction, the Secondary Reaction of this invention is conducted to acylate any unreacted amines. Again, the resulting acylated amines are innocuous and need not be removed from the reaction product, since they are acceptable for incorporation into colorless detergent compositions and are not, themselves, oxidized to undesirable materials by chance reactions with any residual $H_2O_2$ present therein.

The following describes the reactants and reaction conditions for the overall process.

By "substantially water-free" or like terminology used herein is meant that all reactants, solvents, catalysts and apparatus are employed in as water-free state as is reasonably possible. Typically, solvents may be dried using molecular sieves; apparatus is swept dry with dry gas; reactants preferably contain the minimum possible amount of water. Typically, the moisture content of the reactants, solvents, etc., will be in the range of 0.2%, more preferably 0.1%, or less.

By "substantially free of nickel" herein is meant that the N-alkylamino polyol used in the Primary Reaction contains no more than about 20 parts per million (ppm) nickel, and preferably less than about 5 ppm nickel ($Ni^{++}$). Nickel can be conveniently measured by conventional atomic absorption spectroscopy, using diluted samples (5/1 dilution to minimize interference).

By "reducible compounds" or "reducibles" herein is meant chemical compounds which contain reducing sugars either in their natural state or as an adduct with the amine such as N-methylglucamine. Such compounds include, but are not limited to, species such as glucose, fructose, maltose, xylose, N-methylglucosylamine, N-methylfructosylamine, N-methyl-N-glucosylglucamine. This is measured by g.c. analysis.

By "g.c. analysis" herein is meant gas-liquid chromatography ("g.l.c.") using Hewlett-Packard 5890 Series 2 on column injection using DB1 15 meter $0.25\mu$ film thickness ID $250\mu$.

By "improved color" and/or "improved color stability" herein is meant the Gardner Color of the N-alkylamino polyol reactant used in the present process. Moreover, the Gardner Color of the fatty amide surfactants which are subsequently made therefrom is also substantially improved.

By "Gardner Color" herein is meant the standard Gardner measurement known in the art. A Gardner Color reading near zero (solution) represents a nearly colorless ("water-white") solution. Gardner Colors in the 4-7 range are only marginally acceptable for the N-alkylamino polyol reaction products, and it is preferred to achieve Gardner Colors below about 4, preferably 0 to about 2. Of course, use of sugars having low Gardner Colors (e.g., 0 or 1, i.e., water-white syrups) will help ensure that N-alkylamino polyols having desirably low Gardner Colors will be produced. Stated otherwise, use of low (0–2) Gardner Color sugars (preferably white solids or water-white solutions) and use of the reaction sequence disclosed herein results in low Gardner Color N-alkylamino polyols (white or slightly off-white solids).

By "improved odor" herein is meant that the odor character of the reaction product is substantially free of amine or "fish" type odor (once any excess N-alkylamine is removed) and also substantially free of typical browning sugar odors.

By "nickel catalyst" herein is meant any of the conventional Raney nickel or "supported" nickel catalysts well-known in the art. Conventional nickel under the trademark RANEY NICKEL 4200 (Grace Chemicals) is quite suitable for use herein. RANEY NICKEL 3200, (Grace Chemicals); G-96B and G-49A and G-49C are also suitable. While not intending to be limited by theory, it is believed that removing oxides of nickel from the catalyst prevents or impedes dissolution of nickel ions into the reaction milieu, and thus results in the formation of reaction products having a desirable low nickel content. Moreover, it has been found that the nickel catalyst pretreated with pressurized hydrogen can be re-used in multiple subsequent reactions, thereby yielding a substantial overall cost savings.

By "pressurized hydrogen" or "hydrogen pressure" in the polyhydroxy amine-forming reaction herein is meant: for treatment of the nickel catalyst typically 500 psig–5,000 psig; for reaction of the N-alkylamine and sugar (steps c and d below), typically 200 psig–5,000 psig.

By "sugars" in the polyhydroxy amine-forming reaction herein is meant reducing sugars such as glucose, fructose, mannose, lactose, maltose, xylose and the like. The term "sugars" herein also includes glyceraldehyde. Such "sugars" include plant syrups such as cane syrups, corn syrups, potato starch-derived sugar syrups, hydrolyzed wood pulp-derived sugars and the like. High fructose, high glucose and high maltose syrups are economical and preferred, especially if their Gardner Color is satisfactory.

By "N-alkylamines" in the polyhydroxy amine-forming reaction herein is meant compounds such as the N-methyl, N-ethyl, N-propyl, etc., $C_1$–$C_{10}$ N-alkyl amines, and the corresponding hydroxy-substituted amines, e.g., ethanolamine. The $C_1$–$C_3$ alkylamines are preferred, and N-methylamine is most preferred.

By "amine reactant" in the optional reaction to reduce fatty acid levels herein is meant $C_1$–$C_4$ amines and alkanolamines, examples of which include monoethanolamine (preferred), propylamine, ethylamine, 3-amino-1,2-propanediol, 1-amino-2-propanol, 3-amino-1-propanol, tris-(hydroxymethyl)aminoethane, 2-amino-2-ethyl-1,3-propanediol, ammonia, and the like.

By "free fatty acids" herein is meant the fatty acids per se, or salts thereof, e.g., sodium salts, i.e., soaps.

By "residual nascent source of fatty acids" herein is meant, for example, unreacted fatty acid ester starting materials, complex ester-amides which unavoidably form in small amounts during the Primary Reaction, and any other potential source of free fatty acid. It will be appreciated by the chemical formulator that during the overall reaction, work-up and storage of the polyhydroxy fatty acid amide surfactants, such nascent sources of fatty acids can break down in the presence of water in even modestly basic or acidic conditions to release the undesired fatty acids.

By "cyclized by-products" herein is meant the undesirable reaction by-products of the Primary Reaction wherein it appears that the multiple hydroxyl groups in the polyhydroxy fatty acid amides can form ring structures which are, in the main, not readily biodegradable. It will be appreciated by those skilled in the chemical arts that the preparation of the polyhydroxy fatty acid amides herein using the di- and higher saccharides such as maltose will result in the formation of polyhydroxy fatty acid amides wherein linear substituent Z (which contains multiple hydroxy substituents and which is more fully defined hereinafter) is naturally "capped" by a polyhydroxy ring structure. Such materials are not cyclized by-products, as defined herein.

By "acid anhydrides" used in the Secondary Reaction herein is meant the well-known class of materials of the general formula

wherein $R^3$ and $R^4$ can each be hydrocarbyl or substituted hydrocarbyl groups. $R^3$ and $R^4$ may be the same or different (so-called "mixed" anhydrides). $R^3$ and $R^4$ may be combined to form a cyclic anhydride. Low molecular weight anhydrides wherein $R^3$ and $R^4$ are each $C_1$–$C_5$ hydrocarbyl, or, when cyclized, form a $C_4$–$C_6$ oxygen-containing anhydride ring structure, are typical. As noted above, acetic anhydride ($R^3 = R^4 = CH_3$) is a preferred low molecular weight anhydride for use herein. Cyclic anhydrides such as succinic anhydride and glutaric anhydride are further examples of low molecular weight anhydrides useful herein. Unsaturated compounds such as maleic anhydride and glutaconic anhydride constitute other examples of low molecular weight anhydrides useful herein. Other useful anhydrides include compounds wherein $R^3$ and $R^4$ together comprise an aromatic substituent, e.g., compounds such as phthalic anhydride. When conducting the Secondary Reaction herein using an aqueous solvent, the formulator will typically select an anhydride which is quickly miscible or soluble and have a low melting point; hence, acetic anhydride is typically chosen.

FORMATION OF N-ALKYLAMINO POLYOL RAW MATERIAL

The preparation of the N-alkylaminol polyols used in the present process can be conducted in any well-stirred pressure vessel suitable for conducting hydrogenation reactions. In a convenient mode, a pressure reactor with a separate storage reservoir is employed. The reservoir (which, itself, can be pressurized) communicates with the reactor via suitable pipes, or the like. In use, a stirred slurry of the nickel catalyst is first treated with hydrogen to remove traces of nickel oxides. This can be conveniently done in the reactor. (Alternatively, if the manufacturer has access to an oxide-free source of nickel catalyst, pretreatment with $H_2$ is unnecessary. However, for most manufacturing processes some trace of oxides will inevitably be present, so the $H_2$ treatment is preferred.) After removal of excess slurry medium (water) the N-alkyl amine is introduced into the reactor. Thereafter, the sugar is introduced from the storage reservoir into the reactor either under hydrogen pressure or by means of a high pressure pumping system, and the reaction is allowed to proceed. The progress of the reaction can be monitored by periodically removing samples of the reaction mixture and analyzing for reducibles using gas chromatography ("g.c."), or by heating the sample to about 100° C. for 30–60 minutes in a sealed vial to check for color stability. Typically, for a reaction of about 8 liters (ca. 2 gallons) size the initial stage (to 95% of reducibles being depleted) requires about 60 minutes, depending somewhat on catalyst level and temperature. The temperature of the reaction mixture can then be raised to complete the reaction (to 99.9% of the reducibles being depleted).

In more detail, the process for preparing N-alkylamino polyols by reacting an N-alkylamine with a reducing sugar in the presence of a nickel catalyst under hydrogen pressure preferably will comprise:

(a) removing substantially all oxides of nickel from the nickel catalyst (conveniently, this can be done by contacting the nickel catalyst with hydrogen, typically under pressure and temperature of 50°–185° C. at 500–1,500 psig hydrogen);

(b) admixing the nickel catalyst from (a) with the N-alkylamine to provide mixture (b) under hydrogen pressure prior to admixture with the sugar;

(c) admixing the sugar with mixture (b) under hydrogen pressure;

(d) conducting the reaction of the sugar with the N-alkylamine/nickel catalyst mixture (b) at a temperature below about 80° C. and under hydrogen pressure (typically at least 250 psig, preferably at least 500 psig) until at least about 95% by weight of the reducible compounds are no longer present in the reaction mixture;

(e) continuing the reaction, optionally at a temperature of up to about 120° C., until at least about 99.9% by weight of the reducible compounds are no longer present in the reaction mixture; and (f) recovering the N-alkylamino polyol, preferably without purification.

A typical process is wherein the nickel catalyst level is in the range of from about 5% to about 50%, most typically about 10% to about 30%, by weight of the sugar reactants, for optimal throughput. Preferably step (d) of the process is carried out at a temperature of from about 40° C. to about 70° C. Step (e) is preferably carried out at a temperature from about 80° C. to about 120° C. The metal catalyst should be kept under a hydrogen atmosphere if it is desired to use it in repeat batches.

The above process thus affords a convenient reaction for the preparation of compounds which include, but are not limited to, N-alkyl glucamine, N-alkyl fructamine, N-alkyl maltamine or N-alkyl glycerol amine, comprising the steps of:

(a) admixing a nickel catalyst which is substantially free of oxides of nickel with an N-alkylamine (preferably N-methylamine);

(b) under hydrogen pressure, admixing an aqueous solution of glucose, fructose, maltose or glyceraldehyde, respectively, with the mixture from step (a);

(c) allowing the mixture from step (b) to react at a temperature of from about 40° C. to about 70° C. until at least about 95% by weight of the reducible compounds are no longer present in the reaction mixture; and (d) allowing the reaction from step (c) to continue at a temperature below about 120° C. until at least about 99.9% by weight of the reducible compounds are no longer present in the reaction mixture.

Preferably the process is conducted with said catalyst being present at the 10% to 30% level relative to sugar.

When preparing 1,2-propanediol derivatives (e.g., N-alkyl glycerol amines) the formulator may elect to react an N-alkylamine with, for example, 3-chloro-1,2-propanediol or glycidol, at room temperature to about 65° C., typically in ethanol or water.

PRIMARY REACTION TO FORM POLYHYDROXY FATTY ACID AMIDES

The Primary Reaction herein for preparing polyhydroxy fatty acid amide surfactants, comprises reacting a member selected from the group consisting of, preferably, fatty acid esters with an N-alkylamino polyol. In a preferred process, the fatty acid ester is a $C_{10}$–$C_{18}$ alkyl or alkenyl fatty acid methyl ester and the N-alkylamino polyol is selected from N-methyl glucamine, N-methyl fructamine, N-methyl maltamine and N-methyl glycerol amine.

The amide-forming Primary Reaction herein can be illustrated by the formation of N-lauroyl N-methyl glucamine, as follows.

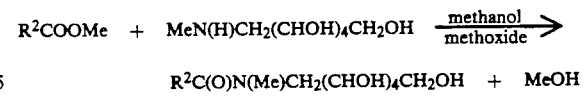

wherein $R^2$ is $C_{11}H_{23}$ alkyl.

More generally, the process herein can be used to prepare polyhydroxy fatty acid amide surfactants of the formula:

$$R^2-\overset{O}{\underset{||}{C}}-\underset{\underset{R^1}{|}}{N}-Z \qquad (I)$$

wherein: $R^1$ is hydrocarbyl, especially $C_1$–$C_4$ hydrocarbyl, as well as hydroxy-hydrocarbyl, 2-hydroxyethyl, 2-hydroxypropyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{31}$ hydrocarbyl moiety, preferably straight chain $C_7$–$C_{19}$ alkyl or alkenyl, more preferably straight chain $C_9$–$C_{17}$ alkyl or alkenyl, most preferably straight chain $C_{11}$–$C_{19}$ alkyl or alkenyl, or mixture thereof, or wherein $R^2$ can include hydroxy-substituted materials such as ricinoleic acid or synthetic fatty acid mixtures available from the catalytic oxidation of paraffinic hydrocarbons or by oxidation or carboxylation of ethylene-growth compounds; and Z is a polyhydroxyhydrocarbyl moiety having a linear hydrocarbyl chain with at least 2 (in the case of glyceraldehyde) or 3 hydroxyls (in the case of other reducing sugars) directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2(CHOR')$(CHOH)$—$CH_2OH$, where n is an integer from 1 to 5, inclusive, and R' is H or a cyclic mono- or poly- saccharide, and alkoxylated derivatives thereof. Most preferred are glycityls wherein n is 4, particularly —CH$_2$(-CHOH)$_4$—CH$_2$OH.

In Formula (I), R$^1$ can be, for example, N-methyl, N-ethyl, N-propyl, N-isopropyl, N-butyl, N-isobutyl, N-2-hydroxy ethyl, or N-2-hydroxy propyl.

R$^2$—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, 2,3-dihydroxypropyl (from glyceraldehyde), etc.

The following reactants, catalysts and solvents can conveniently be used herein, and are listed only by way of exemplification and not by way of limitation.

Reactants — As noted above, various fatty ester reactants can be used herein, but fatty methyl esters are most preferred. Various other fatty esters can be used in the Primary Reaction, including mono-, di- and tri-esters (i.e., triglycerides). Methyl esters are convenient and commercially available with low Gardner Color, and ethyl esters, and the like are all quite suitable. The polyhydroxyamine reactants include N-alkyl and N-hydroxyalkyl polyhydroxyamines with the N-substituent group such as CH$_3$—, C$_2$H$_5$—, C$_3$H$_7$—, HOCH$_2$CH$_2$—, and the like. As noted above, such materials preferably are substantially free of nickel catalysts. Mixtures of the ester and mixtures of the polyhydroxyamine reactants can also be used.

Catalysts — The catalysts used in the Primary Reaction are basic materials such as the alkoxides (preferred), hydroxides — if provision is made to remove water from it and polyhydroxyamine prior to addition of ester — carbonates, and the like. Preferred alkoxide catalysts include the alkali metal C$_1$–C$_4$ alkoxides such as sodium methoxide, potassium ethoxide, and the like. The catalysts can be prepared separately from the reaction mixture, or can be generated in situ using an alkali metal such as sodium. For in situ generation, e.g., sodium metal in the methanol solvent, it is preferred that the other reactants not be present until catalyst generation is complete. The catalyst typically is used at 0.1-10, preferably 0.5-5, most preferably 5 mole percent of the ester reactant. Mixtures of catalysts can also be used.

Solvents —The organic hydroxy solvents used in the Primary Reaction include methanol, ethanol, glycerol, 1,2-propanediol, 1,3-propylene glycol, and the like. Methanol is a preferred alcohol solvent and 1,2-propanediol (propylene glycol) is a preferred diol solvent. Mixtures of solvents can also be used.

General Reaction Conditions — As noted, it is desired to prepare the products of the Primary Reaction (amidation) while minimizing the formation of cyclized by-products, ester amides and color bodies. Reaction temperatures below about 135° C., typically in the range of from about 40° C. to about 100° C., preferably 60° C. to 90° C., are used to achieve this objective, especially in batch processes where reaction times are typically on the order of about 90 minutes, or even up to 3 hours. Most preferably, this reaction is conducted at 85° C. Somewhat higher temperatures can be tolerated in the early stage of the process, especially in continuous processes where residence times can be shorter. All reactants, catalysts, solvents, etc. should be substantially dry. For example, the fatty esters and N-methyl glucamine preferably contain less than about 0.1% water. The concentration ranges of the reactants and solvent provide, for example, what can be termed a "70% concentrated" (with respect to reactants) reaction mixture. This 70% concentrated mixture provides excellent results, in that high yields of the desired polyhydroxy fatty acid amide product are secured rapidly. Indeed, indications are that the reaction is substantially complete within one hour, or less. The consistency of the reaction mixture at the 70% concentration level provides ease of handling. However, even better results are secured at the 80% and 90% concentration levels. However, at the higher concentrations the reaction systems are somewhat more difficult to work with, and require more efficient stirring (due to their thickness), and the like, at least in the early stages of the reaction. However, once the reaction proceeds to any appreciable extent, the viscosity of the reaction system decreases and ease of mixing increases. In one mode, product yields can be increased a few percent by allowing the reaction mixture to "age" (even to solidify) a few hours or days to allow final traces of starting materials to react at lower temperatures.

PREPARATION OF POLYHYDROXYAMINE REACTANT

Catalyst Treatment — Approximately 300 mls of RANEY NICKEL 4200 (Grace Chemicals) is washed with deionized water (1 liter total volume; 3 washings) and decanted. The total catalyst solids can be determined by the volume-weight equation provided by Grace Chemicals, i.e., [(total wt. catalyst+water) — (water wt. for volume)]×7/6=Nickel solids.

308.21 g. of the catalyst Ni solids basis are loaded into a 2 gallon reactor (316 stainless steel baffled autoclave with DISPERSIMAX hollow shaft multi-blade impeller from Autoclave Engineers) with 4 liters of water. The reactor is heated to 130° C. at 1400–1600 psig hydrogen for 50 minutes. The mixture is cooled to room temperature at 1500 psig hydrogen and left overnight. The water is then removed to 10% of the reactor volume using an internal dip tube.

Reaction — The reactants are as follows. 881.82 mls. 50% aqueous monomethylamine (Air Products, Inc.; Lot 060-889-09); 2727.3 g. 55% glucose syrup (Cargill; 71% glucose; 99 dextrose equivalents; Lot 99M501).

The reactor containing the H$_2$O and Raney nickel prepared as noted above is cooled to room temperature and ice cold monomethylamine is loaded into the reactor at ambient pressure with H$_2$ blanket. The reactor is pressurized to 1000 psig hydrogen and heated to 50° C. for several minutes. Stirring is maintained to assure absorption of H$_2$ in solution.

The glucose is maintained in a separate reservoir which is in closed communication with the reactor. The reservoir is pressurized to 4000 psig with hydrogen. The glucose (aqueous solution) is then transferred into the reactor under H$_2$ pressure over time. (This transfer can be monitored by the pressure change in the reservoir resulting from the decrease in volume of the sugar solution as it is transferred from the reservoir into the main reactor. The sugar can be transferred at various rates, but a transfer rate of ca.100 psig pressure drop per minute is convenient and requires about 20 minutes for the volume used in this run. An exotherm occurs when the aqueous sugar solution is introduced into the reactor; the 50° C. internal temperature raises to ca. 53° C.

Once all the glucose has been transferred to the reactor the temperature is maintained at 50° C. for 30 minutes. Hydrogen uptake is monitored by a pressure gauge. Stirring is continued throughout at 800–1,100 rpm or greater.

The temperature of the reactor is increased to 60° C. for 40 minutes, then to 85° C. for 10 minutes, then to 100° C. for 10 minutes. The reactor is then cooled to room temperature and maintained under pressure overnight. The reaction product dissolved in the aqueous reaction medium is conveniently recovered by using an internal dip tube with hydrogen pressure. Particulate nickel can be removed by filtration. Preferably, an internal filter is used to avoid exposure to air, which can cause nickel dissolution. Solid N-methyl glucamine is recovered from the reaction product by evaporation of water.

The foregoing procedure can be repeated using fructose as the sugar to prepare N-methyl fructamines.

The foregoing procedure can al so be repeated using glyceraldehyde as the sugar to prepare N-methyl glycerol amine (3-methylamino-1,2-propanediol).

CONVERSION OF POLYHYDROXY AMINE TO POLYHYDROXY FATTY ACID AMIDE SURFACTANT REACTION PRODUCT AND OPTIONAL MINIMIZATION OF NASCENT FATTY ACIDS

As the initial step, the substantially water-free N-methyl glucamine prepared above is reacted with fatty acid methyl esters to prepare the corresponding fatty acid amides of N-methyl glucamine in the manner disclosed above and in the experimental details, hereinafter. It will be appreciated that coconut fatty acid methyl esters, palm oil fatty acid esters, tallow fatty acid esters, oleyl esters, polyunsaturated fatty acid esters, and the like, can all be used in this reaction, and various N-alkyl polyols, e.g., N-methyl fructamine, N-methyl maltamine, etc., can be used in place of the N-methyl glucamine.

The optional reaction to reduce the levels of nascent fatty acids can thereafter be carried out using primary alkyl amines or alkanolamines. However, it will be appreciated by the chemist that, since alkyl amines generally have undesirable odors, as compared with alkanolamines, it is preferred to employ the alkanolamines. Moreover, the resulting fatty acid alkanolamides can remain in the final product since they serve to boost sudsing rather than diminish it, as do the nascent and free fatty acids. Thus, this intermediate step is useful to the formulator of high sudsing compositions such as hand dishwashing liquids, shampoos and other personal cleansing detergents.

Moreover, while secondary amines will function adequately to remove the nascent sources of fatty acids, such amines can, themselves, form undesirable oxidation products. Accordingly, the primary amines, especially the primary alkanolamines such as ethanolamine ("mono-ethanolamine") are much preferred for use in the optional, fatty acid reducing reaction herein. If this optional step is used, the formulator will recognize that the amount of acylation reactant used in the Secondary Reaction herein may also optionally be increased in a proportionate amount to remove traces of unreacted amine, if any.

It will be further appreciated that it is desirable that the optional fatty acid/amine reaction herein be carried out quickly, such that decomposition of the desired polyhydroxy fatty acid amide surfactant is kept to a minimum. In essence, the optional reaction is an amidation reaction, and seems to be potentiated and accelerated by having a solvent supportive of nucleophilic reaction present. Since methanol is such a solvent, and is also one of the preferred solvents for use in the Primary Reaction herein, it suffices quite well to also act as the solvent optional amidation reaction. Preferably, at least about 6–8% by weight of such solvent which is supportive of nucleophilic reactions, especially methanol , is used in the optional amidation reaction, as well as some 1,2-propanediol. 1,2-propanediol, alone, can also serve as the solvent, but does not appear to be quite as effective as when methanol is present. Other lower alcohols, such as ethanol and iso-propanol, could also be used, but may be poorer choices than methanol or mixtures of methanol/1,2-propanediol. Under such circumstances, some minimal loss (ca. a 1% decrease in overall yield) of polyhydroxy fatty acid amide surfactant may be unavoidable, but this is usually an acceptable trade-off if the decrease in fatty acids in the final product is desired.

The reaction temperature for the optional amidation reaction should preferably be about 85° C., or below, typically in the 65° C.–85° C. range. It will be appreciated that use of excessively high temperatures may desirably speed the amidation, but will undesirably begin to cause cyclization of the polyhydroxy fatty acid amides. While temperatures up to about 120° C. might be tolerable for short periods of time, it would, of course, be undesirable to decrease nascent fatty acid content at the expense of increasing the level of cyclized by-product. The following further illustrates the Primary Reaction with the optional amidation step to decrease the fatty acids.

Apparatus: 500 ml three necked flask, paddle stirrer, reflux condenser with drying tube, thermometer reaching into reaction and a gas inlet tube. The flask is heated with a thermostatted oil bath.

PRIMARY REACTION

The apparatus is predried under nitrogen sweep, cooled and the sweep is shut off. A tare weight is taken without the condenser. Pure powdered N-methylglucamine ("NMG") 97.5 g (0.5 mole), 107 g (0.5 mole) 95% methyl dodecanoate and 18.9 g propylene glycol (solvent) are placed into the flask; the moisture content of each reactant is preferably low, i.e., in the 0.1%–0.3% range or lower, and the solvent is dried over molecular sieves. The mixture is heated to 68° C. with stirring to give a viscous paste; 5.4 g (0.025 mole) 25% sodium methoxide in methanol is then added. The time is taken as zero, and the reaction then brought quickly to 85° C., and held at 85° C. with continuous stirring, and held under nitrogen, no vacuum, no nitrogen sweep. Within 5 minutes a thin milky suspension is formed which clears to a homogeneous clear low viscosity liquid at 55 minutes. During this reaction no reflux is observed, although methanol evolution is calculated to reach 9.1% at complete amidation with NMG. At 150 minutes, the weight of the reaction is within 2 g of initial; a small sample is taken.

OPTIONAL REACTION TO DECREASE FATTY ACIDS

Immediately following the Primary Reaction, 7.6 g (0.125 mole) of dry ethanolamine is added. Vacuum/nitrogen sweep is then applied as stirring and temperature are maintained. At the 210 minute point the vacuum reaches 11 psi (4 psi absolute). Weighing indicates about 1.5 to 2% of reaction weight in excess of theoretical removal of all methanol from catalyst and ester. The resulting product has the following analysis and is suitable for use in high sudsing detergent compositions.

|  | GC Area % | Calculated Concentrations |
|---|---|---|
| Methyl ester | 0.1% | 0.1% |
| Fatty acid/soap | 0.3% | 0.2% |
| NMG | 6.5% | 5.5% |
| Monoethanol amide | 2.6% | 2.2% |
| Total glucoseamide | 89.9% | 76.4% |
| $C_{10}$ | 1.1% | 0.9% |
| $C_{12}$ | 87.6% | 74.5% |
| $C_{14}$ | 1.2% | 1.0% |
| Ester amide | 0.1% | 0.1% |
| Assumed components not observed in GC |  |  |
| Propylene glycol |  | 10.0% |
| Methanol |  | 2.0% |
| Monoethanolamine |  | 3.0 |
| TOTAL |  | 99.5% |

SECONDARY REACTION — ACYLATION OF RESIDUAL AMINES, ESPECIALLY N-ALKYLAMINO POLYOLS

Having thus illustrated an overall process for preparing high quality polyhydroxy fatty acid amides, albeit possibly contaminated with secondary amines, e.g., unreacted N-alkyl polyhydroxy amines, the following illustrates the process of this invention for acylating said amines such that they are no longer susceptible to oxidation with the possible formation of oxidized amino color bodies, hydroxyl amines, nitrosamines, or the like. Since the acylated amino materials formed during the Secondary Reaction are, themselves, innocuous and colorless, they can remain in the finished polyhydroxy fatty acid amide surfactant without need for further purification.

The Secondary Reaction which serves to acylate any unreacted amine, especially N-alkylamino polyol, remaining in the product of the Primary Reaction can be conducted in a melt of the Primary Reaction mixture, or, preferably, in an aqueous solution derived from dissolving the melt in water. Conducting the reaction in water is preferred, since esterification is suppressed. (Of course, minor amounts of alcohol, glycol, etc. solvents from the Primary Reaction can be present.)

For the Secondary Reaction in the melt, the acid anhydride can be added to the melt at ca. 85° C. (The temperature may rise to ca. 100° C., depending on the rate of addition.) The product is dissolved in water and neutralized using sodium hydroxide solution, and can be used in the formulation of detergent compositions without further purification steps.

For the Secondary Reaction in the aqueous solvent, the melt is first dissolved in water, which typically results in an initial solution pH of ca. 12. The anhydride is added, portionwise, from initial pH 12 to about a pH of 7. In order to maintain pH 7, base is added as needed. The temperature throughout this reaction will typically range from 20° C.-50° C., depending on the rate of anhydride addition. The polyhydroxy fatty acid amide surfactant thus prepared is suitable for use in the formulation of detergent compositions without further purification steps.

EXAMPLE I

ACETIC ANHYDRIDE TREATMENT OF PRODUCT (AQUEOUS SOLUTION)

|  | Grams | Moles |  |
|---|---|---|---|
| Reactants (Primary Reaction) |  |  |  |
| N-methyl glucamine (NMG) |  | 97.5 | 0.5 |
| Coconut fatty acid methyl ester (P&G CE1295) | 107.5 | 0.5 |  |
| Propylene glycol | 19.0 |  | 10 wt % |
| 25% sodium methoxide/methanol | 10.8 | 0.05 | 10 mole % |
| Distilled water | 282.5 cc |  |  |
| Reactants (Secondary Reaction) |  |  |  |
| Acetic anhydride | 10.2 | 0.1 | 20 mole % |
| (NMG residual |  | ~0.05) |  |
| 1N sodium hydroxide | 77.5 cc | 0.078 |  |
| Distilled water | 100.0 cc |  |  |
| Absolute ethanol | 25.0 cc |  |  |

The Primary Reaction is run according to the general procedures noted above at 85° C. for 3 hours with vacuum applied during the second half to yield Sample A.

Sample A is immediately poured into water to give a solution at 42° C., pH 12.16. This quenches the Primary Reaction and provides the aqueous solution used in the Secondary Reaction.

In the Secondary Reaction, acetic anhydride and sodium hydroxide are added portionwise with stirring to reach and maintain pH of about 7. After 5 minutes of stirring the reaction mixture becomes a viscous paste, so 100 cc additional water and 25 cc ethanol are added. The resulting mixture is warmed to 40° C. to give a clear thin solution, Sample B (30 minutes elapsed acetylation).

| Relative GC analyses: | A | B |
|---|---|---|
| N-methyl glucamine | 4.1 | <0.1 |
| Linear (uncyclized) glucose amide | 89.3 | 84.1 |
| Fatty acid | 0.3 | 0.4 |
| Ester amide | 1.1 | 0.8 |
| Acetyl NMG |  | 5.7 |

The foregoing procedure is repeated using acetic anhydride at the 10 mole % level with substantially equivalent results.

It will be appreciated by the skilled chemist that the speed and thoroughness of the reaction herein is surprising and unexpected. The pKa of N-alkylamino polyols such as N-methyl glucamine is ca. 9.8. The reaction starts in the basic range, but quickly approaches pH 7. Even at pH 7, the N-methyl glucamine is still being acylated, rather than having the acid anhydride simply "used up" by the concurrent reaction with water.

EXAMPLE II

ACETIC ANHYDRIDE TREATMENT OF PRODUCT (MELT)

|  | Grams | Moles |  |
|---|---|---|---|
| Reactants Primary Reaction) |  |  |  |
| N.-methyl glucamine | 97.5 | 0.5 |  |
| Coconut fatty acid methyl ester (P&G CE1295) | 109.7 | 0.51 |  |
| Propylene glycol | 19.0 |  | 10 wt % |
| 25% sodium methoxide/methanol | 10.8 | 0.05 | 10 mole % |
| Reactants (Secondary Reaction) |  |  |  |

-continued

|  | Grams | Moles |
|---|---|---|
| Acetic anhydride | 10.2 | 0.10 20 mole % |
| (NMG residual | | ~0.05) |
| Materials (Subsequent Work-up) | | |
| Distilled water | 565.0 cc | |
| 1N sodium hydroxide | 70.0 cc | 0.070 |
| 1N hydrogen chloride | 14.0 cc | 0.014 |

The Primary Reaction is run at 85° C. for 5 hours with vacuum applied during the second half to remove most of the solvent. This gives Sample A.

Acetic anhydride is added to the polyhydroxy fatty acid amide amidation product (fluid melt), with stirring, allowed to exotherm to 100° C., and maintained at 85° C. for an additional 30 minutes. This gives Sample B.

The reaction mixture is poured into water to give a solution at pH 4.9. Sodium hydroxide and hydrogen chloride are added with stirring to reach and maintain pH 7.3. This gives Sample C.

A portion of Sample C is bottled and allowed to stand at room temperature over the weekend. This gives Sample D.

Relative GC analyses:

|  | A | B | C | D |
|---|---|---|---|---|
| N-methyl glucamine | 3.5 | 0.1 | 0.1 | 0.2 |
| Linear glucose amide | 92.5 | 82.7 | 81.1 | 82.6 |
| Unreacted methyl ester | 1.1 | 1.0 | 1.0 | 1.0 |
| Fatty acid | 0.1 | 0.1 | 0.1 | 0.1 |
| Ester amide | 0.3 | 1.5 | 1.2 | 1.3 |
| Acetyl NMG | — | 4.3 | 4.3 | 4.4 |

EXAMPLE III

The reaction of Example II is conducted using maleic acid anhydride and phthalic anhydride, respectively, at the 10 mole percent level, to replace the acetic anhydride.

The following is intended to illustrate the use of the polyhydroxy fatty acid amide surfactants made in accordance with this invention in liquid detergent compositions, but is not intended to be limiting thereof. Solid detergent compositions can be prepared by simply dry-mixing otherwise conventional detergent ingredients. Water-soluble $Ca^{++}$ or $Mg^{++}$ salts, e.g., $MgSO_4$, $MgCl_2$ or the like can be used to introduce such cations into the compositions.

EXAMPLE IV

Clear, colorless light duty liquid detergent compositions which are especially adapted for dishwashing and other hard surface cleaning operations are as follows. In the Examples A-D, the surfactants comprise various alkyl ethoxy sulfate surfactants which, using standard terminology, are abbreviated to indicate their average degree of ethoxylation; thus $C_{12-13}EO(0.8)$ sulfate indicates a sulfated mixed $C_{12}-C_{13}$ alcohol fraction having an average degree of ethoxylation of 0.8. These anionic ethoxy sulfates are preferably used in their $Na^+$ or $NH_4^+$ salt form. The $C_{12-13}$ amine oxide is a mixed $C_{12-13}$ (average) dimethyl amine oxide. The $C_{12-14}$ AP betaine is $C_{12/14}H_{25/29}CONH(CH_2)_3N^+(CH_3)_2$—$CH_2CO_2H$. The $C_{12-14}$ AP sultaine is $C_{12}/C_{14}H_{25/29}CONH(CH_2)_3N^+(CH_3)_2CH_2C$-$H(OH)CH_2SO_3H$. The $C_{12-14}$ DM betaine is $C_{12/14}H_{25/29}N^+(CH_3)_2CH_2CO_2H$. The ethoxylated nonionic surfactant designated $C_{9-1}EO(8)$ refers to $C_9-C_{11}$ alcohols ethoxylated with an average of 8 moles of ethylene oxide. The $Ca^{++}$ and $Mg^{++}$ cations are conveniently introduced into the compositions as $CaCl_2$ and $MgCl_2$. The Balance of the compositions comprises water and citrate/propylene glycol present in the glucamide surfactant (1–5%) and 1–3% cumene sulfonate or xylene sulfonate hydrotrope. The pH is typically 6.8–7.4 ($NH_4^+$ salts) or 7–8.2 ($Na^+$ salts).

| Ingredient* | Percent (wt.) | | | |
|---|---|---|---|---|
|  | A | B | C | D |
| $C_{12-14}$ N-methyl glucamide | 11 | 8 | 12.7 | 9 |
| $C_{12-13}EO(0.8)$ sulfate | — | 16 | 10.0 | 9 |
| $C_{12-14}EO(3)$ sulfate | 11 | — | 2.7 | 14 |
| $C_{12-13}EO(6.5)$ sulfate | — | — | — | 3 |
| $C_{12-14}$ AP betaine | — | — | 2 | — |
| $C_{12-14}$ AP sultaine | — | — | — | 1.0 |
| $C_{12-13}$ amine oxide | 2.5 | — | — | 1.0 |
| $C_{12-14}$ DM betaine | — | 2.0 | — | — |
| $C_{9-1}EO(8)$ | 0.5 | 8 | 7 | — |
| $Ca^{++}$ | — | — | 0.5 | 1.0 |
| $Mg^{++}$ | 0.9 | 0.25 | — | — |
| Balance | Bal | Bal | Bal | Bal |

*Commercial grade surfactants may be bleached to colorless (i.e., to provide water-clear liquids). The $C_{12-14}$ N-methylglucamide as prepared herein contains 0.1% or less of N-methylglucamine.

What is claimed is:

1. In a process for preparing a polyhydroxy fatty acid amide surfactant by reacting a fatty acid ester and an N-alkylamino polyol said surfactant containing undesirable amounts of unreacted N-alkylamino polyol, the improvement which comprises dissolving said surfactant containing said unreacted N-alkylamino polyol in water and adding thereto an acid anhydride to acylate said unreacted N-alkylamino polyol, whereby the total level of unreacted N-alkylamino polyol present in said surfactant is substantially eliminated.

2. A process according to claim 1 wherein the acid anhydride is low molecular weight acid anhydride.

3. A process according to claim 2 wherein the acid anhydride is a member selected from the group consisting of acetic anhydride, maleic anhydride and succinic anhydride.

4. A process according to claim 1 wherein the reaction with the acid anhydride is carried out at a temperature from about 10° C. to about 85° C.

5. A clear, colorless detergent composition which comprises colorless ingredients and a polyhydroxy fatty acid amide which is prepared according to claim 1 and which is substantially free from N-alkylamino polyols.

* * * * *

UNITED STATES PATENT AND TRADEMARK OFFICE
CERTIFICATE OF CORRECTION

PATENT NO. : 5,298,636
DATED : March 29, 1994
INVENTOR(S) : D. S. Connor and M. H. K. Mao It is certified that error appears in the above-indentified patent and that said Letters Patent is hereby corrected as shown below:

Column 14, line 41, insert

"Unreacted methyl ester     1.7     <0.1".

Signed and Sealed this

Eighteenth Day of July, 1995

*Attest:*

BRUCE LEHMAN

*Attesting Officer*     *Commissioner of Patents and Trademarks*